US010595712B2

(12) United States Patent
Chen et al.

(10) Patent No.: US 10,595,712 B2
(45) Date of Patent: Mar. 24, 2020

(54) ADAPTIVE OPTICAL LASER BEAM STEERING THROUGH ENDOSCOPE FOR LASER SURGERY IN KIDNEY

(71) Applicant: University of Pittsburgh—Of the Commonwealth System of Higher Education, Pittsburgh, PA (US)

(72) Inventors: Peng Kevin Chen, Washington, PA (US); Tatum Varut Tarin, Pittsburgh, PA (US); Bryan L. Nelsen, Pittsburgh, PA (US); Botao Zhang, Gilbert, AZ (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 141 days.

(21) Appl. No.: 14/520,078

(22) Filed: Oct. 21, 2014

(65) Prior Publication Data

US 2015/0112144 A1 Apr. 23, 2015

Related U.S. Application Data

(60) Provisional application No. 61/893,843, filed on Oct. 21, 2013.

(51) Int. Cl.
*A61B 1/00* (2006.01)
*G02F 1/29* (2006.01)
(Continued)

(52) U.S. Cl.
CPC ...... *A61B 1/00172* (2013.01); *A61B 1/00167* (2013.01); *G02B 23/2469* (2013.01); *G02B 26/06* (2013.01); *G02B 27/0927* (2013.01); *G02B 27/0988* (2013.01); *G02F 1/2955* (2013.01); *A61B 1/307* (2013.01)

(58) Field of Classification Search
CPC . A61B 1/00172; A61B 1/00167; A61B 1/307; G02F 1/2955; G02B 26/06; G02B 27/0927; G02B 27/0988; G02B 23/2469
See application file for complete search history.

(56) References Cited

U.S. PATENT DOCUMENTS

| 6,210,401 B1 * | 4/2001 | Lai | B23K 26/0624 |
| | | | 351/209 |
| 2003/0076571 A1 * | 4/2003 | MacAulay | G02B 21/0028 |
| | | | 359/237 |

(Continued)

OTHER PUBLICATIONS

Neff, John A., et al.; Two Dimensional Spatial Light Modulators: A Tutorial ; Proceedings of the IEEE, vol. 78, No. 5 (May 1990), pp. 826-855.*

(Continued)

*Primary Examiner* — John P Leubecker
*Assistant Examiner* — Genja M Frankert
(74) *Attorney, Agent, or Firm* — Klarquist Sparkman, LLP

(57) ABSTRACT

A lightguide is configured to transmit a scanned and/or focused processing beam to a target. The processing beam has a wavefront amplitude and phase set by a spatial light modulator. Suitable wavefront characteristics are obtained based on portions of the processing beam returned to a detector through the lightguide. A beam path can be detected at a first, reduced power, and processing along the beam path performed at a second, higher optical power.

26 Claims, 7 Drawing Sheets

FIG. 2

(51) Int. Cl.
*A61B 1/07* (2006.01)
*G02F 1/01* (2006.01)
*G02B 23/24* (2006.01)
*G02B 26/06* (2006.01)
*G02B 27/09* (2006.01)
*G02F 1/295* (2006.01)
*A61B 1/307* (2006.01)

(56) References Cited

U.S. PATENT DOCUMENTS

| | | | | |
|---|---|---|---|---|
| 2010/0056928 A1* | 3/2010 | Zuzak | ................. | A61B 5/0071 600/476 |
| 2010/0059490 A1* | 3/2010 | Unrath | ............... | B23K 26/0613 219/121.73 |
| 2011/0064113 A1* | 3/2011 | Ando | .................. | H01S 3/0804 372/99 |
| 2011/0137126 A1* | 6/2011 | French | ............... | A61B 1/00165 600/178 |
| 2011/0182529 A1* | 7/2011 | Kempe | ............. | G01N 21/6458 382/274 |
| 2012/0070817 A1* | 3/2012 | Wang | .................. | A61B 5/0059 435/3 |
| 2014/0064654 A1* | 3/2014 | Anand | ............... | G02B 21/0032 385/3 |
| 2014/0128743 A1* | 5/2014 | Yew | ................... | A61B 1/00172 600/476 |
| 2014/0303504 A1* | 10/2014 | Stankovic | ............. | A61B 1/227 600/476 |
| 2016/0018786 A1* | 1/2016 | Matsumoto | ........ | G01N 21/6458 359/9 |

OTHER PUBLICATIONS

Bagnoud et al. Independent phase and amplitude control of a laser beam by use of a single-phase-only spatial light modulator; Optics Letters, vol. 29, Issue No. 3, Feb. 1, 2004; pp. 295-297.*

Booth, M. J. Adaptive optical microscopy: the ongoing quest for a perfect image. Light Sci. Appl. 3, e165 (2014).*

* cited by examiner

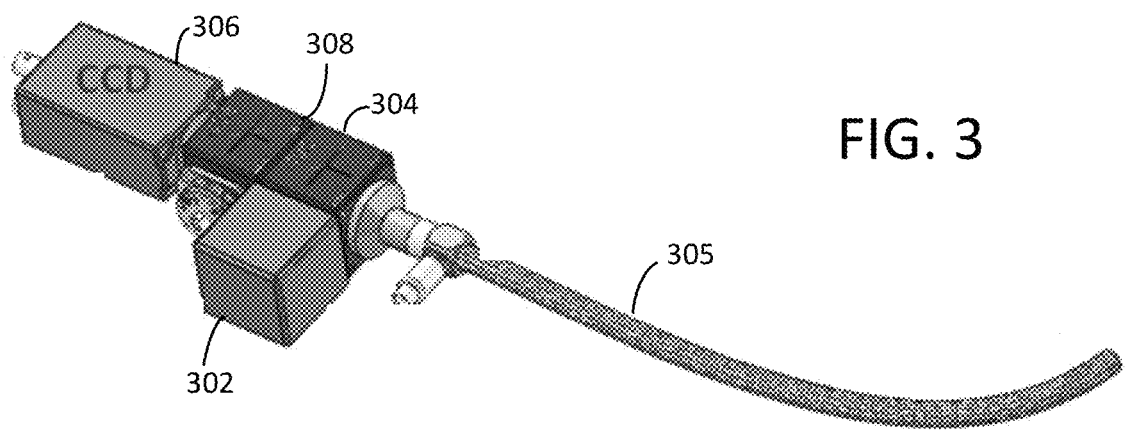
FIG. 3
FIG. 4A
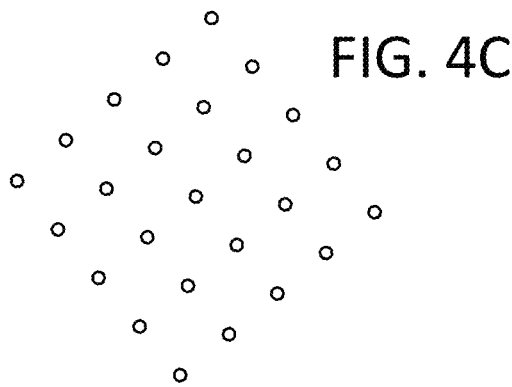
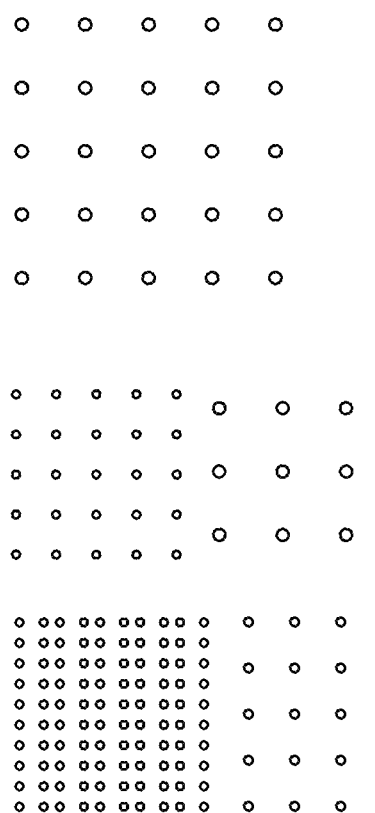
FIG. 4C
FIG. 4D
FIG. 4B

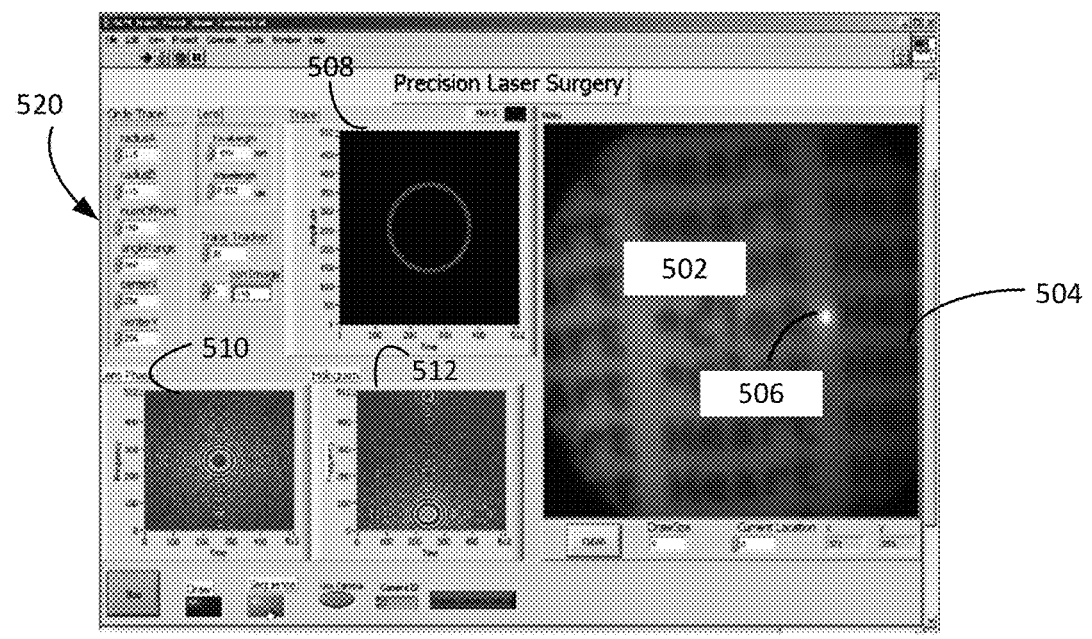
FIG. 5A
FIG. 5B
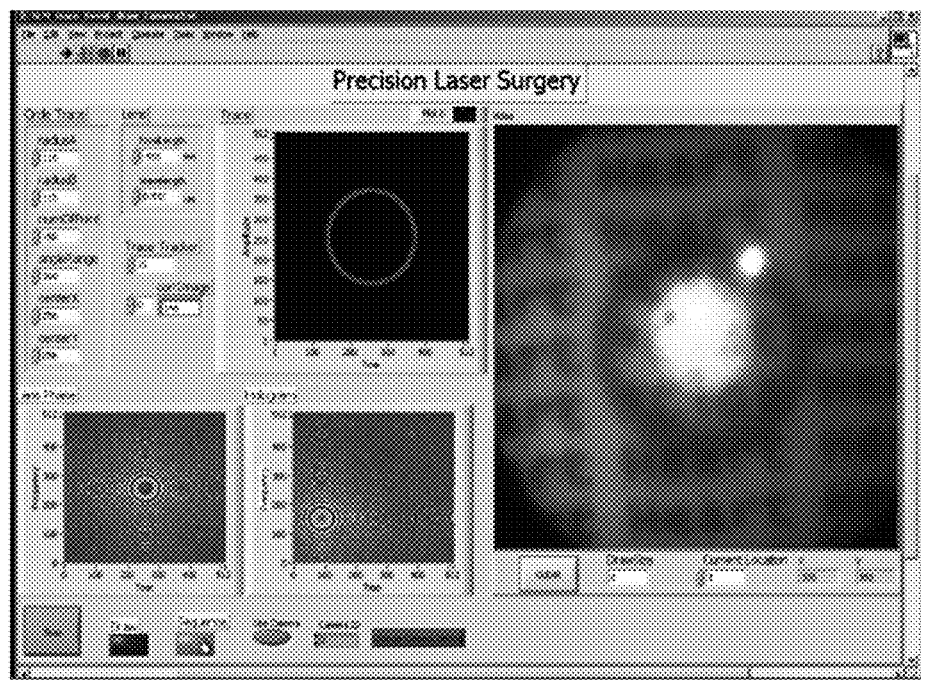

FIG. 7A
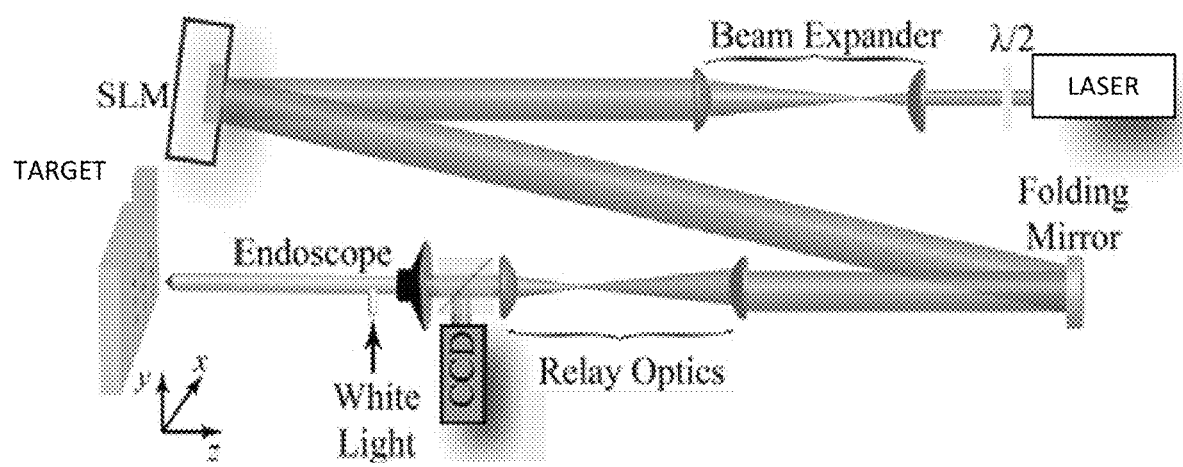
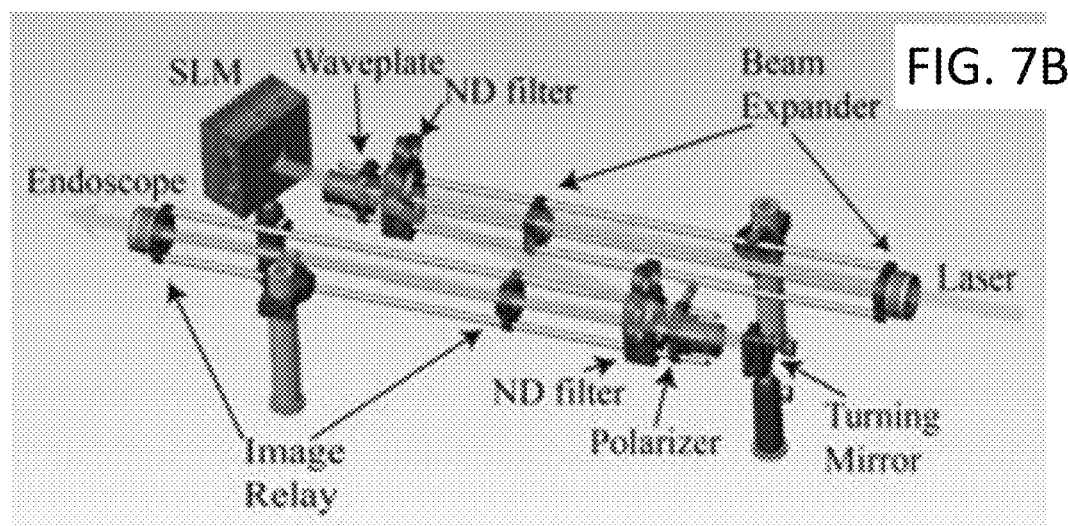
FIG. 7B

US 10,595,712 B2

ADAPTIVE OPTICAL LASER BEAM STEERING THROUGH ENDOSCOPE FOR LASER SURGERY IN KIDNEY

CROSS REFERENCE TO RELATED APPLICATION

This application claims the benefit of U.S. Provisional Application 61/893,843, filed Oct. 21, 2013, which is incorporated herein by reference.

FIELD

The disclosure pertains to endoscopes.

BACKGROUND

The development of endoscopic ureteroscopy has allowed for the treatment of ureteral and renal pelvis diseases such as nephrolithiasis, ureteral stricture, uretero-pelvic junction obstruction and upper tract transitional cell carcinoma, through a minimally invasive approach. Ureteroscopy is generally performed in the operating room under general anesthesia. Typically, a cysto scope is inserted into the bladder and the ureteral orifice is identified in order to gain access to the upper urinary tract. The inner diameter of the ureter generally measures approximately 3 mm. The ureteral orifice is accessed using flexible wires which can be passed up into the renal pelvis. A ureteroscope can then be passed over the wire and guided up the ureter to the renal pelvis. This may be accomplished under direct visualization or with fluoroscopic guidance.

Due to the size restraints of accessing the upper urinary tract, ureteroscope size has been limited to 8 French or approximately 3 mm in outside diameter. A ureteroscope typically includes three channels, including an optical channel for endoscope imaging (~1 mm diameter); a fiber light source (~0.5 mm diameter), and a working channel for laser fiber insertion and irrigation. After accounting for the required optics and light source, a flexible ureteroscope allows for only a single working channel of approximately 1 mm. Unfortunately, this single working channel must accommodate irrigation to allow for visibility and the passage of a laser fiber in order to either destroy kidney stone or ablate tissue. The size of the working channel poses limitations to the treatment of upper urinary tract disease. The passage of the laser fiber through the small working channel severely impedes irrigation flow and thus limits visibility. Additionally, the passage of a semi-stiff laser fiber inhibits deflection of the tip of the ureteroscope and thus limits the ability to treat all areas of the urinary collecting system.

Conventional uteroscopes require passing a laser fiber through the working channel which impedes irrigation flow and deflection of the ureteroscope tip. To counteract lower irrigation flows, high pressure irrigation has been utilized. However, visualization can still be affected. Smaller flexible holmium laser fibers (200 micron) have been utilized. However, these fibers still affect deflection and irrigant flow and are fragile. Given the confines of the upper urinary tract system and limitations to current technologies, there exists a clinical need for a novel system to access the entire upper urinary tract that allows improved irrigation flow, a larger working channel, and unimpeded tip deflection to access difficult areas of the renal pelvis.

BRIEF DESCRIPTION OF THE DRAWINGS

FIG. 3 is a perspective view of a representative endoscope that is configured to permit SLM based beam scanning.

FIGS. 4A-4D illustrate structured irradiation and beam steering patterns obtained with SLM based adaptive optics.

FIGS. 5A-5B illustrate a user interface for display and control of beam steering and focusing.

FIG. 7A illustrates structured light generation through an endoscope.

FIG. 7B illustrates Fourier relay optics.

DETAILED DESCRIPTION

Figure 1:
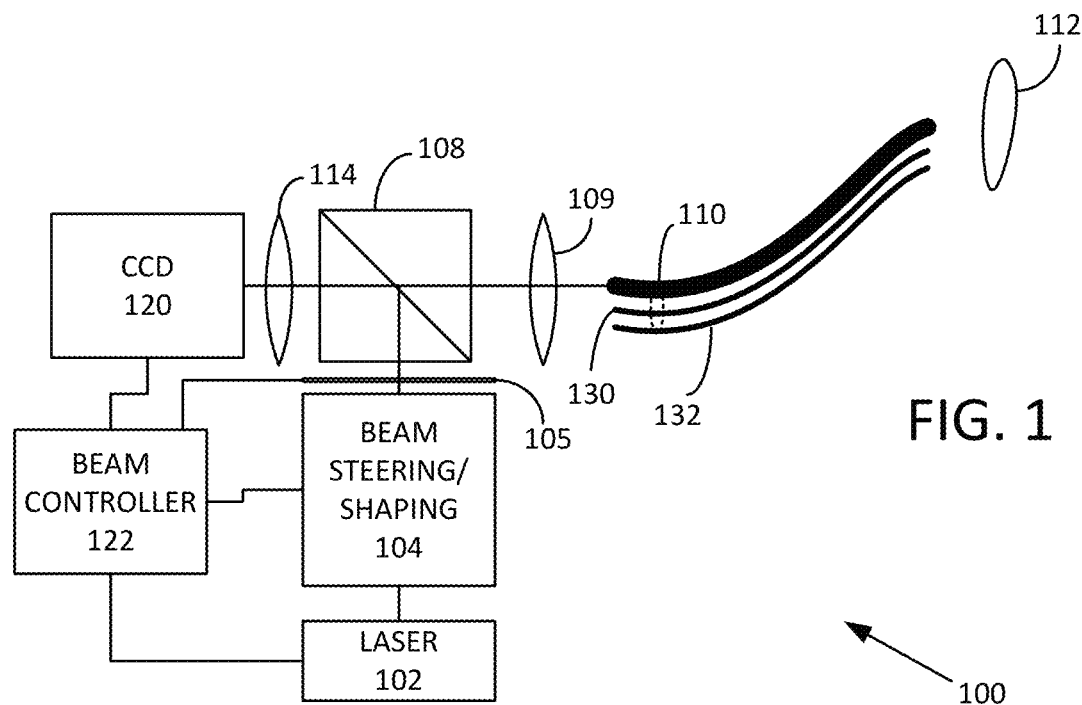
FIG. 1 is a schematic illustration of an endoscope that includes a spatial light modulator (SLM) configured for beam steering and focusing.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

Using an adaptive optical element, a working beam from a surgical laser source can be sent through an optical channel used for endoscope imaging. This scheme can completely open a working channel for irrigation. By sculpting the wave front of the surgical laser source adaptively using a spatial light modulator, the on-target focal point, divergence, and on-target shape of an ablation laser spot can be actively controlled through the endoscope. In addition, the working beam can be steered within the field-of-view of the endoscope without movement of the endoscope. The combined focal point selection and laser beam steering can be controlled with a computer system. Using the same beam forming and scanning techniques, on-target Raman spectroscopy and Coherent Anti-Stokes Raman spectroscopy can be performed to determine cancer margins or otherwise investigate a specimen.

FIG. 1 illustrates a representative endoscope 100 that includes a laser 102 configured to provide a working beam to a beam steering and shaping system 104. A beam controller 122 is coupled to the beam steering shaping system 104 so as to establish a wavefront distribution of the working beam corresponding to a selected wavefront phase and amplitude. Such wavefronts can be selected to focus or otherwise distribute beam power at a target surface, and such power distributions can be time varying based on time-varying phase or amplitude variations applied by a spatial light modulator. Such a beam is referred to herein as an adapted beam.

The adapted beam is directed to a beam splitter 108 and an optical system 109 and then into a lightguide 110 for delivery to a target 112 as a target beam. Based on the applied wavefront curvature, a target beam can be focused, scanned, or otherwise shaped and situated. For example, the target beam can be focused at a surface of the target 112 and scanned about a selected target location. An imaging detector 120 and objective lens 114 are situated to receive an imaging beam from the lightguide 110, so as to form an image of the target 112. An optical attenuator 105 is situated so that working beam power can be reduced while an intended beam path is traced by the beam controller 122, prior to applying higher beam power to process or treat the target 112. In other examples, the beam controller 122 is coupled to the laser 102 so as to reduce laser power.

In some examples, a lumen 130 is situated adjacent or coupled to the light guide 110 and extends along the lightguide 110 so as to couple fluids to and from a region near the specimen 112, or to otherwise provide access to the target 112. An optical fiber 132 can be similarly situated to provide an illumination beam for target imaging. Typically, the lightguide 110 is a coherent fiber bundle. In some examples, a beam shaping and steering system can be situated so that the imaging beam is processed to permit imaging through a fiber bundle that is not a coherent fiber bundle.

Figure 2:
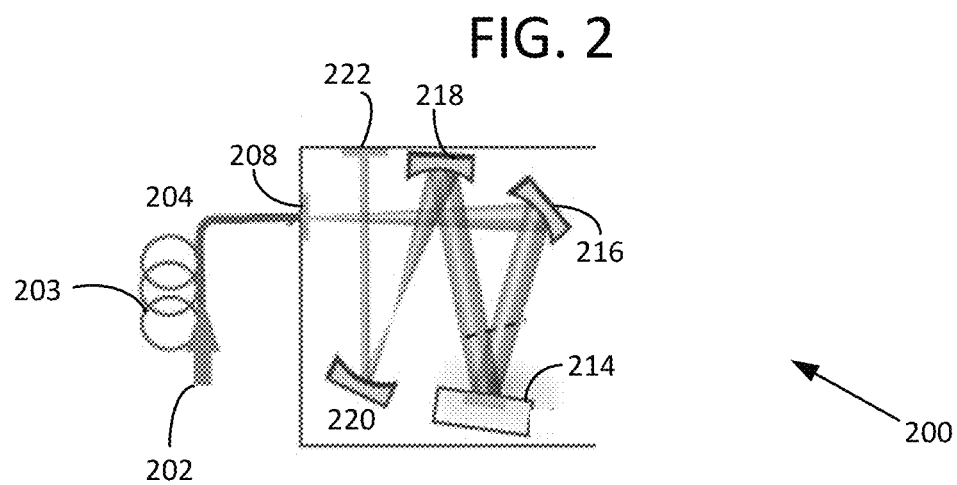
FIG. 2 illustrates a representative adaptive optical system for beam steering and focusing.

FIG. 2 illustrates a representative beam shaping/steering system 200. A laser beam 202 is coupled to an optical fiber 203 and directed through a window 208 to a first mirror 216, a reflective spatial light modulator (SLM) 214, a second mirror 218, and a third mirror 220. A processed beam exits via a window 222. The SLM can be a reflective or transmissive SLM, and can be configured to establish a selected beam wavefront, i.e., a distribution of amplitude and phase. A variety of SLM types can be used, including deformable mirror or liquid crystal devices. Control of the SLM 214 is generally based on optical beam portions returned from a target so that the phase and amplitude of the beam delivered to a lightguide produce a selected beam profile and location at the target, and permit scanning of a processing beam at a target.

FIG. 3 is a perspective view of a representative endoscope. An adaptive optics system 302 is configured to couple an adapted beam via beamsplitter module 304 to a lightguide that is part of a probe arm 305. In addition, a CCD or CMOS camera 306 is coupled to the lightguide via a beamsplitter module 308 and the beamsplitter module 304. The beam splitter module 308 can be configured to direct an illumination beam from a light source to an illumination fiber in the probe arm 305. Typically, the probe arm 305 also includes a working channel for mechanical 813 access to a target.

FIGS. 4A-4D illustrate representative target beam positions and patterns obtained based on settings of an adaptive optical systems. FIGS. 4A-4C show a variety of beam positions of different spacings and arrangements. FIG. 4D illustrates a beam scan along an elliptical path. The target beam can generally be directed and focused at an arbitrary location.

FIG. 5A illustrates a representative user interface for an endoscopy system. A target image 502 is displayed in a window 504 along with a current location 506. A window 508 illustrates a beam pattern that is to be scanned on a target. Window 510 illustrates a selected distribution of lens phase of a processing beam and window 512 illustrates beam position as a function of time during exposure. A user input area 520 is provided for user definition of beam trace patterns and positions, as well as selection of beam wavelength and an effective focal length associated with SLM applied phases. FIG. 5B illustrates beam positioning on the target during processing.

Figure 6A:
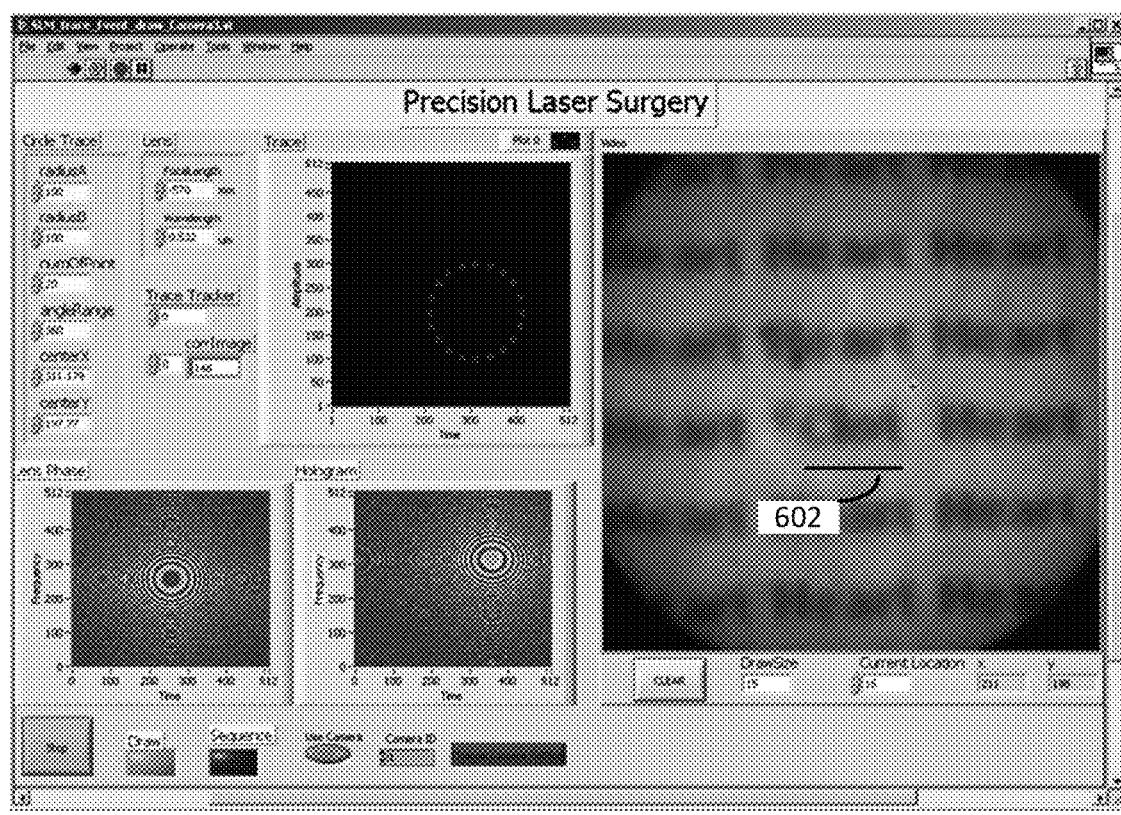
FIGS. 6A-6C illustrate a user interface showing a beam path traced prior to and during treatment.
Figure 6B:
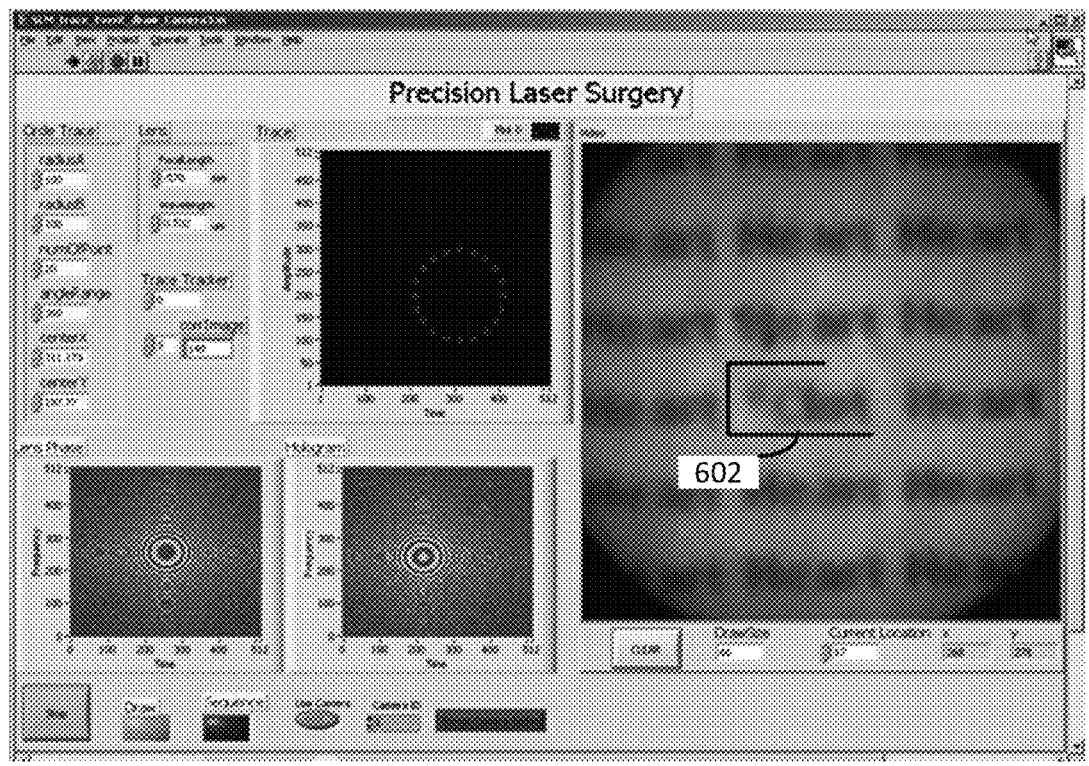
Figure 6C:
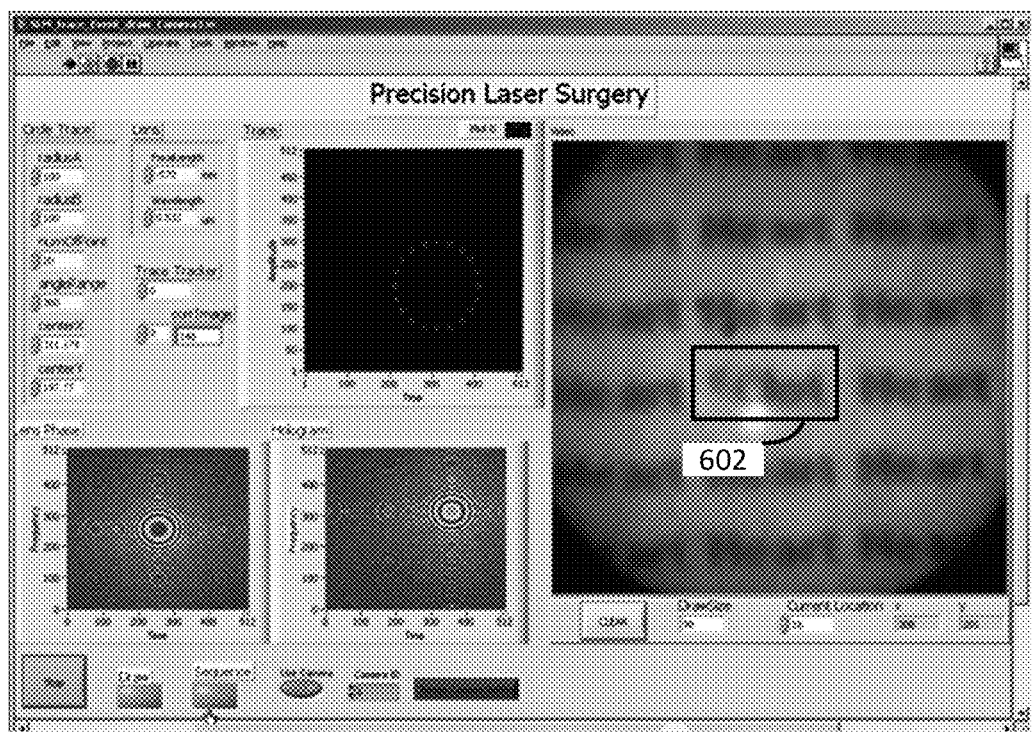

FIGS. 6A-6B illustrate portions of a path 602 on a target as displayed to a clinician. The path 602 is traced by adjustment of an adaptive optical system with a low power beam applied so as to confirm beam pointing. FIG. 6C illustrates tracing path 602 by the processing beam at a power sufficient for treatment.

FIGS. 7A-7B illustrate modification of an ureteroscope system to incorporate an SLM to generate structured light and to steer a laser beam. A single-mode green laser output beam is collimated using a pair of beam expander lenses. Laser polarization and intensity can be controlled by neutral density (ND) filters and a half-wave plate before projection onto the SLM. A computer generated holograph is redirected through a turning mirror into a pair of relay lenses that perform an all-optic Fourier Transform and couple the resulting structured light through the endoscope for 3D imaging. To generate a desired laser beam pattern (or to steer the laser beam to a desired location), the SLM imprints a multiple beam phase pattern (referred as a kinoform) to the input beam wavefront to achieve a desired light pattern. The calculation of the kinoform is not straightforward and usually requires several iterations to find out proper phase information for the SLM. However, this can be done rapidly through a graphic processing unit (GPU) based on an adaptive algorithm. The input electric field can be expressed as:

$$E(\vec{\rho}) = \sum_{j=1}^{N} \epsilon_j \exp(i2\pi j\pi \vec{\rho} r_j \cdot \vec{\rho}/\lambda f) = A(\vec{\rho})\exp(i\varphi\vec{\rho}),$$

wherein f is the effective focal length for the system including the microscope objective and relay optics, $\epsilon_j$ is the electrical field of the $j^{th}$ optical structure at the image plane. When the calculated amplitude is the same as the input laser beam amplitude, the calculated phase is the SLM phase pattern. Based on this algorithm, a laser beam with desired geometric shape and desired steering angle can be projected through the relay optics onto the endoscope to control the laser beam.

Figure 8:
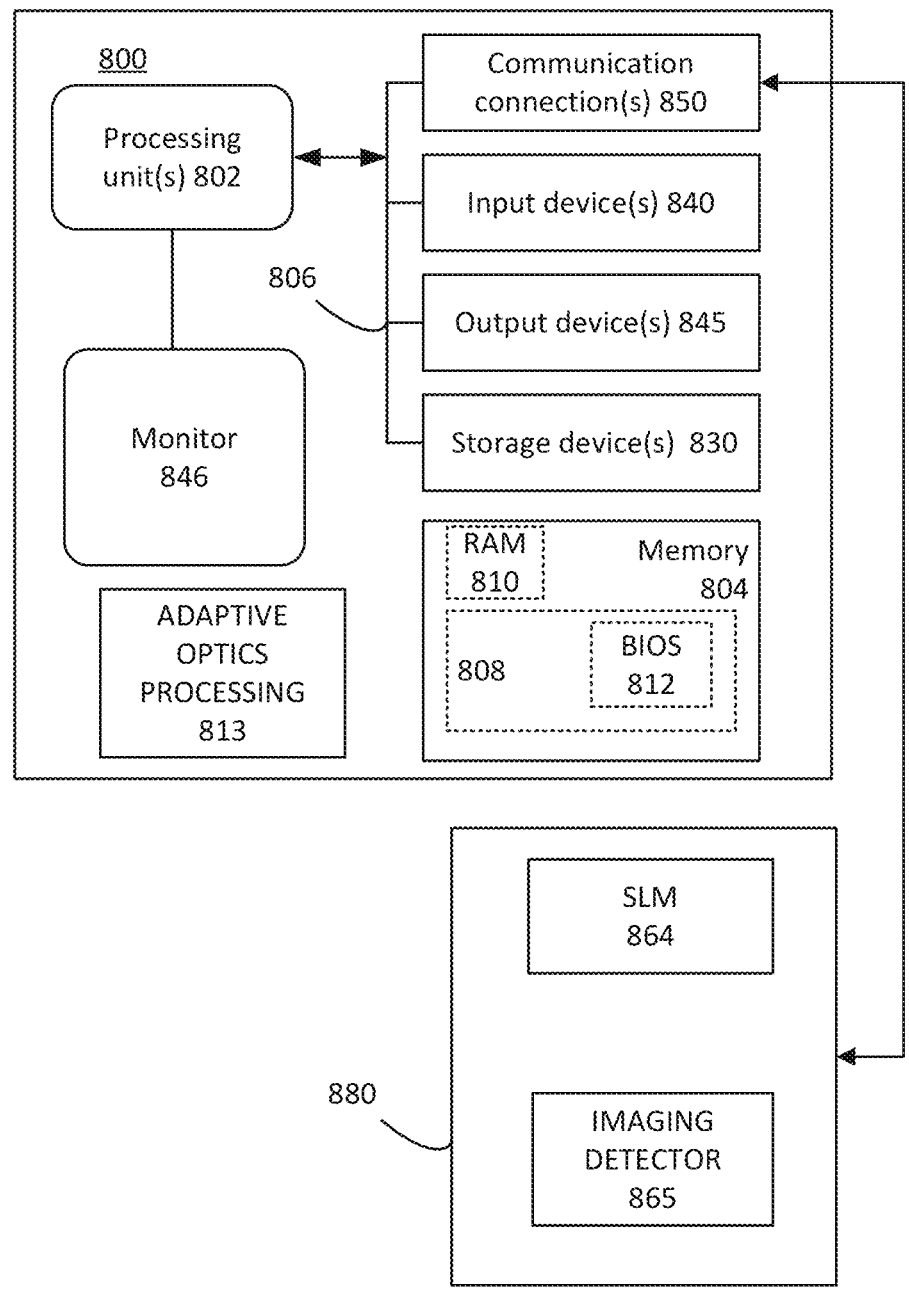
FIG. 8 is a block diagram of a computer controlled endoscope that includes a spatial light modulator.

FIG. 8 and the following discussion are intended to provide a brief, general description of an exemplary computing environment in which the disclosed technology may be implemented. Although not required, the disclosed technology is described in the general context of computer-executable instructions, such as program modules, being executed by a personal computer (PC). Generally, program modules include routines, programs, objects, components, data structures, etc., that perform particular tasks or implement particular abstract data types. Moreover, the disclosed technology may be implemented with other computer system configurations, including hand-held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 8, an exemplary system for implementing the disclosed technology includes a general purpose computing device in the form of an exemplary conventional PC 800, including one or more processing units 802, a system memory 804, and a system bus 806 that couples various system components including the system memory 804 to the one or more processing units 802. The system bus 806 may be any of several types of bus structures including a memory bus or memory controller, a peripheral bus, and a local bus using any of a variety of bus architectures. The exemplary system memory 804 includes read only memory (ROM) 808 and random access memory (RAM) 810. A basic input/output system (BIOS) 812, containing the basic routines that help with the transfer of information between elements within the PC 800, is stored in ROM 808.

The exemplary PC 800 further includes one or more storage devices 830 such as a hard disk drive for reading from and writing to a hard disk, a magnetic disk drive for reading from or writing to a removable magnetic disk, and an optical disk drive for reading from or writing to a removable optical disk (such as a CD-ROM or other optical media). Such storage devices can be connected to the system bus 806 by a hard disk drive interface, a magnetic disk drive interface, and an optical drive interface, respectively. The drives and their associated computer-readable media provide nonvolatile storage of computer-readable instructions, data structures, program modules, and other data for the PC 800. Other types of computer-readable media which can store data that is accessible by a PC, such as magnetic cassettes, flash memory cards, digital video disks, CDs, DVDs, RAMs, ROMs, and the like, may also be used in the exemplary operating environment.

A number of program modules may be stored in the storage devices 830 including an operating system, one or more application programs, other program modules, and program data. As shown in FIG. 8, an adaptive optical processing module 813 includes computer executable instructions for determined SLM drive signals to produce selected optical beam wavefronts. A user may enter commands and information into the PC 800 through one or more input devices 840 such as a keyboard and a pointing device such as a mouse. Other input devices may include a digital camera, microphone, joystick, game pad, satellite dish, scanner, or the like. These and other input devices are often connected to the one or more processing units 802 through a serial port interface that is coupled to the system bus 806, but may be connected by other interfaces such as a parallel port, game port, or universal serial bus (USB). A monitor 846 or other type of display device is also connected to the system bus 806 via an interface, such as a video adapter. Other peripheral output devices, such as speakers and printers (not shown), may be included. An endoscope 880 is coupled to the PC 800, and includes an SLM 864 and an imaging detector 865.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An apparatus, comprising:
    a spatial light modulator (SLM) situated to receive an input optical beam;
    an SLM controller coupled to the SLM and configured to establish a wavefront phase and amplitude distribution of the input optical beam by adjusting the SLM to apply a phase modulation to the input optical beam to produce an adapted optical beam;
    a fiber bundle having a proximal surface situated to receive the adapted optical beam from the SLM and a distal surface situated to emit the adapted beam from the distal surface as a focused adapted beam that is directed to a target and to receive portions of the focused adapted beam returned from the target;
    a detector optically coupled to the proximal surface of the fiber bundle to the receive portions of the focused adapted beam returned from the target; and
    wherein the phase modulation applied by the SLM to produce the focused adapted beam is determined based on an amplitude of the received portions of the focused adapted beam returned from the target by iterative processing of the wavefront phase established by the SLM.

2. The apparatus of claim 1, wherein the SLM controller is configured to establish the wavefront phase and amplitude distribution so as to direct the focused adapted beam to a selected target location.

3. The apparatus of claim 2, wherein the fiber bundle is a coherent fiber bundle.

4. The apparatus of claim 2, wherein the detector is an imaging detector and further comprising a beam splitter situated to direct an imaging beam from the proximal surface of the fiber bundle to the imaging detector.

5. The apparatus of claim 4, wherein the beam splitter is configured to transmit the imaging beam to the imaging detector.

6. The apparatus of claim 4, wherein the beam splitter is situated to direct the adapted beam from the SLM to the proximal surface of the fiber bundle.

7. The apparatus of claim 2, further comprising a channel situated adjacent the fiber bundle, and extending along a fiber bundle length, and situated to provide a fluid channel extending to the target.

8. The apparatus of claim 1, further comprising a laser system configured to produce and direct the input optical beam to the SLM.

9. The apparatus of claim 2, wherein the SLM controller is configured to determine the selected adapted beam wavefront phase and amplitude distribution based on an amplitude of radiation received from the distal end of the fiber bundle.

10. The apparatus of claim 9, further comprising an adapted beam source and a detector situated to receive portions of the adapted beam from the target, wherein the SLM controller is configured to determine the selected adapted beam wavefront phase and amplitude distribution based on amplitudes of portions of the adapted beam received by the detector from the distal end of the lightguide.

11. The apparatus of claim 10, wherein the detector is an imaging detector situated to receive an imaging beam from the proximal surface of the fiber bundle.

12. The apparatus of claim 11, wherein the SLM is configured to scan the focused adapted beam with respect to a target feature of interest.

13. The apparatus of claim 12, wherein the SLM is configured to scan the focused adapted beam with respect to the target feature of interest as a scanned beam that encircles the target feature.

14. A method, comprising:
directing an optical beam to a spatial light modulator (SLM);
adjusting a wavefront phase of the optical beam with the SLM to produce an adapted beam;
directing the adapted beam at a first power to a fiber bundle so as to emit, from a distal surface of the fiber bundle, the adapted beam at a target, wherein the wavefront phase of the adapted beam is iteratively adjusted by the SLM based on an amplitude of portions of the adapted beam returned by the target so that the adapted beam is emitted from the fiber bundle as a focused beam; and
processing the target by directing the iteratively adjusted, focused beam to the target at a second power that is greater than the first power.

15. The method of claim 14, further comprising scanning the iteratively adjusted focused beam at the target based on adjustment of the wavefront phase of the adapted beam.

16. The method of claim 15, further comprising forming an image of the target based on an imaging beam received from a proximal surface of the fiber bundle.

17. The method of claim 14, wherein the wavefront phase of the adapted beam is adjusted by applying a phase modulation with an SLM phase modulation selected so that an amplitude calculated based on an output adapted beam amplitude at a distal end of the lightguide corresponds to an input adapted beam amplitude at the proximal end of the lightguide.

18. The method of claim 14, wherein the wavefront phase of the adapted beam is adjusted by applying an SLM phase modulation selected so that an amplitude calculated based on an adapted beam amplitude at an image plane associated with the target corresponds to an input beam amplitude.

19. The apparatus of claim 1, wherein the wavefront phase of the adapted optical beam is adjusted by applying, with the SLM, a phase modulation selected so that an amplitude calculated based on a beam amplitude at a distal end of the fiber bundle corresponds to an input beam amplitude at the proximal end of the lightguide.

20. The apparatus of claim 1, wherein the wavefront phase of the adapted optical beam is adjusted by applying, with the SLM, a phase modulation selected so that an amplitude calculated based on a beam amplitude at an image plane associated with the target corresponds to an input beam amplitude.

21. The method of claim 14, wherein an image of the target is formed by directing an imaging beam from a proximal surface of the lightguide to an imaging detector.

22. The method of claim 21, wherein the imaging detector is a CCD.

23. The apparatus of claim 1, further comprising a light source situated to couple an illumination beam to the target.

24. An endoscope, comprising:
a laser situated to produce a processing beam;
a spatial light modulator (SLM) situated to receive the processing beam and produce an adapted beam;
a light source situated to produce an imaging beam;
a beam splitter situated to receive the adapted beam from the SLM and the imaging beam from the light source;
a fiber bundle having a proximal surface and a distal surface, wherein:
the proximal surface is situated to receive the adapted beam and the imaging beam from the beam splitter and emit the adapted beam and the imaging beam to a target at a distal end, and
the distal end is situated to receive portions of the adapted beam and portions of the imaging beam from the target and couple the received portions of the adapted beam and the imaging beam to the proximal end;
an imaging detector situated to receive the portions of the adapted beam from the target from the beam splitter and an imaging beam from the target and produce an image of the target that includes a location of the adapted beam at the target; and
an SLM controller situated to iteratively adjust a phase modulation applied by the SLM to the processing beam based on the portions of the adapted beam received from the target by the imaging detector so that the adapted beam is focused and scanned at the target, wherein the phase modulation is determined based on an amplitude of received portions of the adapted beam returned from the target.

25. The endoscope of claim 24, wherein the laser is operable to produce the processing beam at a first power level to establish the modulation applied by the SLM to produce the adapted beam, and a second power level that is greater than the first to process the target.

26. The endoscope of claim 25, further comprising a display that exhibits the image of the target and the location of the adapted beam at the target.

* * * * *